United States Patent [19]

Lundin et al.

[11] 4,215,683

[45] Aug. 5, 1980

[54] EAR-PLUG

[75] Inventors: Tord R. Lundin, Billesholm; Kalman Csiki, Landskrona, both of Sweden

[73] Assignee: Gullfiber AB, Billesholm, Sweden

[21] Appl. No.: 778,134

[22] Filed: Mar. 16, 1977

[30] Foreign Application Priority Data

Mar. 18, 1976 [SE] Sweden .................. 7603411

[51] Int. Cl.² .......................... A61F 11/02
[52] U.S. Cl. ................................. 128/152
[58] Field of Search ............... 128/152, 151, 140 N, 128/270, 269, 267, 263, 261, 285

[56] References Cited

U.S. PATENT DOCUMENTS

| 2,785,675 | 3/1957 | Berkman | 128/152 |
| 2,785,676 | 3/1957 | Berkman | 128/152 |
| 3,771,521 | 11/1973 | Kittredge | 128/152 |
| 3,791,385 | 2/1974 | Davis et al. | 128/285 X |
| 3,842,166 | 10/1974 | Bucalo | 128/270 X |

FOREIGN PATENT DOCUMENTS

| 619389 | 3/1927 | France . |
| 341238 | 12/1971 | Sweden . |
| 341784 | 4/1972 | Sweden . |
| 438283 | 11/1935 | United Kingdom . |
| 527650 | 10/1940 | United Kingdom . |
| 578613 | 7/1946 | United Kingdom . |

*Primary Examiner*—Henry J. Recla
*Attorney, Agent, or Firm*—Burns, Doane, Swecker & Mathis

[57] ABSTRACT

An ear-plug comprising a plug-like body of fine glass wool and a surrounding casing of thin polyethylene film having low friction vis-a-vis the auditory canal. The glass wool is exposed at the surface of the expanded end of the ear-plug not to be inserted into the auditory canal. The ear-plug is fixed as to shape by means of a circumferential heat weld in the polyethylene film located where the expanded part of the ear-plug begins.

6 Claims, 4 Drawing Figures

EAR-PLUG

BACKGROUND OF THE INVENTION

The present invention relates to protecting ear-plugs of the kind comprising a plug-like body of fibrous material, preferably mineral fiber material, and especially so-called fine glass wool, and a casing which surrounds at least that part of the body which is intended to be inserted into the auditory canal.

A plurality of different ear-plugs of the kind mentioned hereinbefore have already been proposed. The surrounding casing in these earlier cases has been stated to be for example in the form of a thread net, a cotton weave or gauze, preshaped rubber, applied latex or a waxy binder sprayed on in a modelled fashion, and its function is to fix the plug and/or confine the fibrous material, as well as in certain cases to contribute to some extent to an increased attenuation by means of its own inherent sound attenuating effect.

One object of the present invention is to provide an improved ear-plug of the above mentioned kind, which without impairing the degree of comfort it affords when used gives substantially improved sound-attenuation, prevents fibre fragments from being left behind in the auditory canal when the plug is removed after use, and is easy to fix in place. The above object is achieved by virtue of the fact that the ear-plug in accordance with the invention exhibits the features set out in the attached claims.

The ear-plug in accordance with the invention is accordingly characterized substantially in that the casing comprises an external layer giving a substantially lower friction than the fibrous material in the plug-like body. The layer can be completely impervious but since it has been found that this may be experienced as a comfort impairment, it is advantageous to design the layer so that it permits pressure equalization at the time of insertion of the plug into the auditory canal and, possibly, also so that a certain degree of moisture penetration can take place after insertion, although these effects should not mean that any significant change takes place in the frictional properties of the layer. In accordance with the invention, these effects can be achieved in a simple and advantageous manner by arranging that at least that part of the layer which is intended to be introduced into the auditory canal, is provided with cuts permitting the development of passages through the layer as a consequence of differences in pressure between its two sides. The cuts suitably are so arranged that they delimit flaps, tongues or the like in the layer, which, at any increase in pressure between the plug and the ear-drum membrane, associated with the introduction of the plug into the auditory canal, can swing away so that temporary passages are created through which pressure equalization can take place. Moisture in the auditory canal can furthermore diffuse more quickly through the cuts. The friction between the layer and the wall of the auditory canal, in association with the introduction of the plug into the canal, is not afffected by this arrangement since the material in the plug-like body does not come into contact with the auditory canal.

Tests on volunteers have shown that an ear-plug provided with a casing in accordance with the invention surprisingly exhibits a typical increase in acoustic attenuation (in relation to a conventional glass wool plug, not provided with such an envelope but otherwise of identical design) of the order of 7 to 10 dB, which should be with a typical frequency-dependent attenuation of between around 8 and 26 dB for the conventional plug (attenuation measured in accordance with the hearing threshold method).

The reason for the improved acoustic attenuation can be attributed as follows:

To achieve a certain attenuation the plug-like body must contain a certain quantity of material. Furthermore, it is the quantity of material which is contained in the auditory canal, which is decisive in determining the attenuation. By providing the plug-like body with an external surface which has low friction in relation to the auditory canal, the introduction of the plug into the canal is simplified and this means that more material enters the auditory canal with a resultant improvement in sound attenuation. It should be emphasised that in tests the casing has not been found to produce any appreciable inherent attenuation. This has also been confirmed in tests on an artificial auditory canal, in which ear-plugs both with and without an external layer have been inserted for equal distances into the auditory canal without any appreciable difference in sound attenuation being observed.

The lower friction layer can advantageously be made of a thin plastic sheet or foil, for example of the adhesive film kind. Most thermoplastic sheets are suitable for use as the material of the layer. Advantageously polyethylene foil can be used since foil of this kind can be obtained in very thin qualities, is easily weldable, is entirely inert and does not give rise to any allergic reactions. The welding property means that the plug in accordance with the invention can readily be given a fixed shape for example by the use of a circumferential thermal weld in the plastic foil.

BRIEF DESCRIPTION OF THE DRAWING

The invention will be described in more detail hereinafter while referring to the attached drawings, in which

FIG. 4 is a diagram illustrating attentuation graphs obtained in tests, for a conventional ear-plug and an ear-plug in accordance with the present invention.

DESCRIPTION OF THE PRFERRED EMBODIMENT

Figure 1:
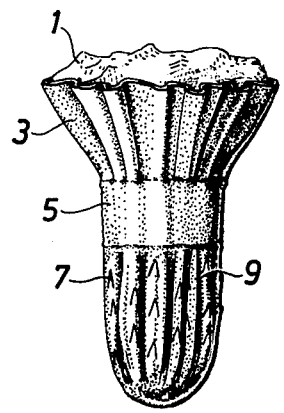
FIG. 1 is a side elevation view of an embodiment of an ear-plug in accordance with the invention.
Figure 2:
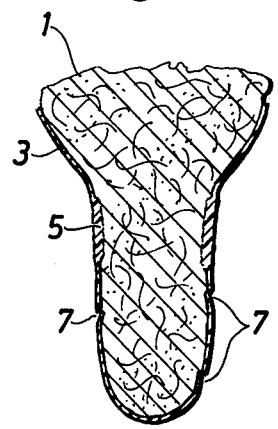
FIG. 2 is a vertical central sectional view of the plug of FIG. 1.

The ear-plug in accordance with the invention, shown in FIGS. 1 and 2, comprises a fibrous, plug-like body 1 of fine glass wool whose substantially cylindrical part, rounded at the end and intended for insertion into the auditory canal, is enclosed within a casing 3 of polyethylene foil having a thickness of around 10 microns. The casing 3 extends also substantially up to the opposite, enlarged end of the body 1, which end is designed to be gripped at the time of insertion of the plug into the auditory canal and thereafter at least partially fill out the concha, the glass wool being exposed at the end surface. The plug is fixed as to shape by arranging that the casing 3, originally flat and swept or wrapped together around the body 1, is provided with a circumferential, band-like heat weld 5 in which the casing 3 is also to a certain extent welded to the glass wool in the body 1. The heat weld 5 is located substantially at the junction between the essentially cylindrical part of the body 1 and the generally funnel-shaped expanded end section of the body 1. The casing 3 is provided, at the cylindrical part of the body, with a plurality of cuts 7 forming pivotal tongues, these providing pressure compensation and making good moisture diffusion possible. Because the casing 3 is swept or crinkled around the body 1, it contains lengthwise creases or folds 9.

It will be appreciated that an ear-plug in accordance with the invention can for example be manufactured in accordance with the method disclosed in Swedish Pat. No. 341,784, the layer of gauze or the like mentioned in the patent specification being replaced by a casing in accordance with the present invention and a heat welding device being arranged in a suitable manner if a heat weld fixing is desired.

Figure 3:
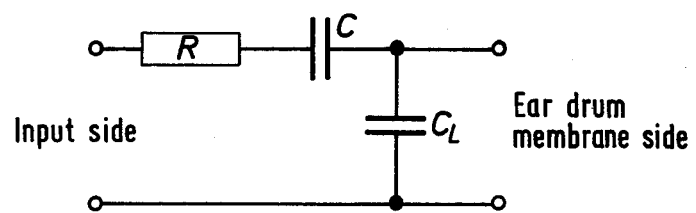
FIG. 3 is a simplified equivalent electrical circuit diagram for an ear-plug.

FIG. 3 illustrates a simplified equivalent electrical circuit diagram for an ear-plug of the kind in question, in which the mass of the plug has been neglected, this being realistic since the mass is only about 0.2 grammes. Considering the notation used in the equivalent circuit diagram, R represents the internal friction of the plug (fibre body), C represents the plug resilience and $C_L$ represents the resilience of the combination of the ear-drum membrane and the air volume between it and the plug. It should be emphasized that the plug can be regarded as a membrane, or in other words diaphragm, having a certain resilience and a certain internal friction, which is arranged in the auditory canal at a point about mid-way to the ear-drum membrane.

The attenuation is thus given by the following formula:

$$\text{Attenuation } (dB) = 20 \log \sqrt{\left(1 + \frac{C_L}{C}\right)^2 + (2\pi f R C_L)^2}$$

From this, it is apparent that the internal friction R of the fibre body and the resilience C of the plug should respectively be as high and as low as possible in order to achieve good attenuation. Howevver, the latter requirement is normally in conflict with the requirement for comfort since low resilience means increased stiffness and therefore associated discomfort.

FIG. 4 illustrates attenuation graphs obtained during tests with a number of volunteers, for conventional fine glass wool plugs without a casing in accordance with the invention (graph A) and for plugs of the same kind with a casing in accordance with the invention (graph B), both plug types for the rest being designed in accordance with figures 1 and 2 (more precisely, around a plunger in a mould, in accordance with the method set out in Swedish Pat. No. 341,784). The attenuation was measured in a free acoustic field in accordance with the hearing threshold method.

Commencing from the attenuation graphs obtained and the above expression for attenuation, the effect of the external layer 5 upon R and C can be calculated very simply. In the case discussed, we thus obtain the following relationships:

$$R_{fibre\ body + layer} \approx 2.6 \cdot R_{fibre\ body}$$
$$C_{fibre\ body + layer} \approx 0.35 \cdot C_{fibre\ body}$$

This thus confirms the fact that by providing an ear-plug with an external layer in accordance with the invention, a plug is obtained which, after insertion int the auditory canal, gives a combination of increased friction and reduced resilience (i e. increased stiffness), which means a substantial increase in sound attenuation for no penalty in comfort.

What is claimed is:

1. An ear protecting plug comprising an elastic, plug-like body of fibrous material, at least a part of said body being adapted for insertion into an auditory canal of an ear, and a casing surrounding at least said part of the body, said casing being adapted for insertion in the auditory canal, having a surface with a friction coefficient substantially lower than that of the fibrous material and being a thin plastic film wherein at least part of the plastic film includes means to permit pressure equalization at the time of introduction of the plug into a canal and to permit penetration of moisture, said means including cuts which permit the formation of passages through the plastic film, the part of the plug-like body being adapted for insertion into an auditory canal of an ear being substantially cylindrical and the plug-like body further including an expanded end part adapted to at least partially fill out the concha of the ear outside the auditory canal, the plastic film being wrapped at least around the part of the plug-like body adapted to be inserted into an auditory canal thereby producing lengthwise folds in the casing, a circumferential heat weld in the plastic film being positioned at the junction of the substantially cylindrical part and the expanded end part to fix the plastic film and weld it to the fibrous material.

2. An ear-plug comprising an elastic, plug-like body of fibrous material and a casing surrounding at least a part of the body adapted for insertion into an auditory canal, the casing including an external layer having a substantially lower coefficient of friction than the fibrous material the plug-like body, wherein at least part of the layer includes means to permit pressure equalization at the time of introduction of the plug into a canal, and means to permit penetration of moisture, wherein the means to permit pressure equalization includes cuts which permit the formation of passages through the layer, the cuts defining tongues in the layer.

3. An ear-plug as claimed in claim 2, wherein the layer is made of a plastic foil.

4. An ear-plug as claimed in claim 3, wherein selective heat welds in the plastic foil fix the shape of the foil and the location of the foil to the fibrous body.

5. An ear-plug as claimed in claim 4, wherein a circumferential heat weld in the plastic foil fixes the shape of the foil and the location of the foil relative to the fibrous body.

6. An ear-plug as claimed in claim 2, the ear-plug being fixed by means of a circumferential heat weld in the plastic film at the junction between a substantially cylindrical part and an expanded end part.

* * * * *